(12) United States Patent
Larichev et al.

(10) Patent No.: US 7,891,812 B2
(45) Date of Patent: Feb. 22, 2011

(54) ABERROMETER PROVIDED WITH A VISUAL ACUITY TESTING SYSTEM

(75) Inventors: Andrey Victorovich Larichev, Moscow (RU); Nikita Georgievich Iroshnikov, Moscow (RU); Artem Jurievich Resnyansky, Moscow (RU)

(73) Assignee: Visionica, Ltd., Moscow (RU)

( * ) Notice: Subject to any disclaimer, the term of this patent is extended or adjusted under 35 U.S.C. 154(b) by 721 days.

(21) Appl. No.: 10/593,613

(22) PCT Filed: Mar. 22, 2005

(86) PCT No.: PCT/RU2005/000124

§ 371 (c)(1),
(2), (4) Date: Jun. 14, 2007

(87) PCT Pub. No.: WO2005/089635

PCT Pub. Date: Sep. 29, 2005

(65) Prior Publication Data

US 2008/0018855 A1  Jan. 24, 2008

(30) Foreign Application Priority Data

Mar. 22, 2004  (RU) .............................. 2004108174

(51) Int. Cl.
*A61B 3/10* (2006.01)
(52) U.S. Cl. .................. 351/211; 351/221; 351/239
(58) Field of Classification Search .................. 351/237, 351/239, 241
See application file for complete search history.

(56) References Cited

U.S. PATENT DOCUMENTS 4,881,807 A  11/1989 Luce et al.
5,562,656 A  10/1996 Sumiya
6,550,917 B1  4/2003 Neal et al.

(Continued)

FOREIGN PATENT DOCUMENTS

GB  1196/1904  5/1904

(Continued)

OTHER PUBLICATIONS

Paul Blanchard et al; Phase Diversity Wave-Front Sensing With a Distorted Diffraction Grating; Applied Optics, vol. 39, No. 35; Dec. 10, 1000; pp. 6649-6655.

(Continued)

*Primary Examiner*—Jordan M. Schwartz
(74) *Attorney, Agent, or Firm*—Holtz, Holtz, Goodman & Chick, PC

(57) ABSTRACT

An aberrometer is provided for automatically measuring a human eye aberration, determining a subjective visual acuity associated with the selection of a best spherocylindrical correction, and investigating the influence of high orders aberrations on the visual acuity. The aberrometer includes a point light source which is projected on the eye retina, scattered back by the retina, and passes through the eye optical systems acquiring a phase modulation corresponding to the total eye optical aberration. The aberrometer also includes a wave front sensor whose output signal is transmitted to a device control system, an aberration compensation system which is disposed between the human eye and the wave front sensor and through which radiation coming out from the eye and projected on the eye retina passes, and a test picture projector which projects the test picture image on the eye retina through the aberration compensation system.

8 Claims, 7 Drawing Sheets

U.S. PATENT DOCUMENTS

| | | | |
|---|---|---|---|
| 6,964,480 B2 * | 11/2005 | Levine | 351/211 |
| 2002/0159029 A1 | 10/2002 | Ross et al. | |
| 2003/0112411 A1 | 6/2003 | Martino | |
| 2003/0193647 A1 * | 10/2003 | Neal et al. | 351/221 |
| 2004/0100619 A1 * | 5/2004 | Olivier et al. | 351/221 |

FOREIGN PATENT DOCUMENTS

| | | |
|---|---|---|
| SU | 1766359 | 10/1992 |
| WO | WO 03/000153 A2 | 1/2003 |

OTHER PUBLICATIONS

J. Christopher Dainty et al; Low-Order Adaptive Deformable Mirror; Applied Optics, vol. 37, No. 21; Jul. 20, 1998; pp. 4663-4668.

J. Liang et al; Objective Measurement of Wave Aberrations of the Human Eye with the Use of a Hartmann-Shack Wave Front Sensor; Optical Society of America; vol. 11, No. 7, Jul. 1994; pp. 1949-1957.

A.V. Larichev et al; Adaptive System for Eye-Fundus Imaging; Quantum Electronics, 2002.

* cited by examiner

ABERROMETER PROVIDED WITH A VISUAL ACUITY TESTING SYSTEM

This application is a U.S. National Phase Application under 35 USC 371 of International Application PCT/RU2005/000124 filed Mar. 22, 2005.

BACKGROUND OF THE INVENTION

1. Field of the Invention

The group of inventions that is the substance hereof concerns the designs and adjustment of aberrometers, ophthalmologic instruments used in medical clinical practice for measuring aberrations of the human eye. The aberrometer presented herein as an invention is intended for automatically measuring aberrations of the human eye and determining subjective visual acuity while, simultaneously, selecting the best spherocylindrical correction in various accommodation statuses of the eye and, in the second modification of the instrument, for researching the influences of higher-order aberrations on subjective visual acuity and making forecasts as to the results of correcting vision with eyeglasses, individual contact lenses, intraocular lenses or laser ablation.

The alignment system of the aberrometer intended for fine-adjusting the distance between the eye and the instrument (the alignment of the entrance pupil of the gage with the pupil of the eye) is its integral part yet may be used, according to its function, with any ophthalmologic instruments used, for instance, in clinics while operating on the human eye, diagnosing its pathological conditions or measuring its characteristics.

The method implemented in the alignment system of the aberrometer may be used for adjusting any ophthalmologic instrument.

2. Description of the Related Art

In clinical practice, visual acuity is determined with the use of tables containing symbols or pictures whose sizes, normally, at a distance of 5 meters, correspond to various angular sizes of their images on the eye retina. The angular size of one minute corresponds to 100% or 1 vision (20/20 in English language literature). A tested person estimates the smallest size of the symbols he or she can discern, which is the indication of his or her visual acuity. For instance, if the size of still discernible symbols corresponds to the angle of 5 minutes, the visual acuity is 50% (0.5). The best spherocylindrical correction is determined using exchangeable test lenses (phoroptors) while continuously checking the results against the test table. The process is rather tedious and lengthy, especially in the case of complicated astigmatism (see E. I. Kovalevsky, *Ophthalmology*, Moscow, Medicine publishers, 1995, pp. 45-83). The selection of correction lenses may be accelerated through various methods of measuring refraction such as retinoscopy or the use of automatic refractometers. These instruments indicate the initial parameters of test corrective lenses. Aberrometers are more advanced instruments measuring the optical characteristics of the eye. They not only measure refraction and astigmatism but also higher-order aberrations.

There is a device with the same function as the invention that is the substance of this application (the Aberrometer with a System for Testing Visual Acuity). It is an ophthalmologic instrument described in *Objective Measurement of Wave Aberrations of the Human Eye with the Use of a Hartmann-Shack Wave-front Sensor* by Junzhong Liang, Bernhard Grimm, Stefan Goelz and Josef F. Bille (JOSA A, Volume 11, Issue 7, July 1949, 1994) intended for measuring aberrations of the human eye. It contains a point light source. When projected on the retina, its light creates a virtual reference source whose radiation is diffracted by the retina and, while passing through the optical systems of the eye, becomes phase-modulated in accordance with the combined optical aberrations of it, then goes through the system measuring the shape of the wavefront of the light leaving the eye. The system is a Shack-Hartman's sensor whose output signal goes to the instrument's controls, including a computer that processes the data, restores the aberration chart, stores the data and controls the instrument following its operator's commands. We used this device as a prototype because the sum total of its significant characteristics makes it the closest to the one that is the substance of this application—in its both modifications.

While measuring aberrations, an increased dynamic range, that is, the best ratio between the maximal and minimal aberration values may not be achieved with the use in the device of the Shack-Hartman's wavefront sensor because it does not allow measuring aberrations with large and small amplitudes equally well. If the parameters of the sensor are selected so as to increase the range of measurement, small aberrations are measured with considerable errors. Because both small and large aberrations occur in clinical practice, this factor is a serious disadvantage of aberrometers equipped with such sensors.

There are various methods of increasing the dynamic range of measurement of wavefront sensors.

For instance, there is a technical solution (U.S. Pat. No. 6,550,917) suggesting the use of a special pre-compensation reference beam creating a small-diameter light spot on the retina. When this is done, the image of the reference beam in the focus of the micro-lens matrix will also be small. Yet when the light spot on the retina is small, the influence of phase and amplitude speckle modulation increases, which results in a lower precision of measurements. Besides, when a probing beam of a considerable diameter is used, the conditions requiring a single-pass measurement are not met and certain aberrations self-compensate during the second pass of the beam. When the diameter of the probing beam is small, between 0.5 mm and 0.8 mm, the size of the light spot on the retina is practically independent of the aberrations of the eye and the system of pre-compensation becomes mostly redundant. However, refraction compensation may be used in cases of large refraction errors (>10 D). Such system is necessary for the light beam coming out of the eye because its diameter may be as large as 8 mm.

The same invention (U.S. Pat. No. 6,550,917) suggests that the system of pre-compensation placed between an optical projection system and the eye include a device adding cylindrical correction to the probing beam. In this case, it is also suggested that the diameter of the light spot on the retina be minimal. It is believed that this increases the precision of determining the coordinates of spots, because the spots in the focus of the micro-lens matrix are the images of the light spot on the retina. Yet this is true only when the coordinates of the spots are determined against the maximal intensity dot. At this time, in practically all such instruments, a different algorithm is used (see the Liang et all prototype) where coordinates of the spots are determined by calculating their mass centers (according to their intensity). This method allows to calculate the location of the spot with a precision exceeding the distance between the light-sensitive elements of matrix light detectors such, for instance, as those used in CCD cameras. Moreover, this precision increases as the area of the spot on the light detector increases. So when such algorithms are used, there is no need to make the light spot on the retina small. On the contrary, its excessive smallness leads to the loss of precision.

The same invention suggests that a cylindrical telescope be used to introduce astigmatic correction. The disadvantages of such system include their functional limitation because cylindrical instead of astigmatic wavefront is produced. There are also their complicated mechanical controls. The explicit use of astigmatic instead of cylindrical corrector is far more convenient. Astigmatism may be transformed into a cylinder by adding defocusing, that is, compensating the curvature of one of the cross-sections of the saddle. As is known, defocusing and astigmatism are orthogonal functions while defocusing and cylinder are not. This is why an expansion by such functions of the shape of a wavefront is univalent. Accordingly, if an execution unit, that is, an astigmatic corrector implements these functions, it makes the automatic control of such a device much simpler.

There is a device for compensating astigmatism (see L. S. Urmakher and L. I. Aizenshtat, *Ophthalmologic Instruments*, 1988, p. 288) that includes two systems rotating around the optical axis, cylindrical or toric lenses of different signs and mechanically engaged manual controls. A disadvantage of this astigmatism correcting device is that it may not be controlled automatically because its mechanical drive is too complicated, the rotation of the said lenses being mutually dependent (their turning angles are equal, while the axis of the instrument is adjusted by turning the whole device around its optical axis).

Because there is no test pattern projector in this prototype, the device is not suitable for testing visual acuity and for subjectively assessing the quality of and controlling the correction.

Another disadvantage of the instrument is the lack in it of a self-testing capability and of the automatic calibration of its mechanical and optical elements in order for the instrument to remain in a usable condition.

During the use, the moving mechanical elements of aberrometers may go out of their working positions. Moreover, the adaptive elements (mirrors) are generally non-linear. For instance, in piezo-controlled mirrors, non-linearity and hysteresis reach 25% of the control range. This is why the results of the use of control signals for estimating correction profiles become incorrect. The known aberrometers are calibrated with optical test elements. These are either external systems optically analogous to the eye or similar devices built into the optical system of the instrument and using beam-splitting plates (U.S. Pat. No. 6,637,884). External calibrating systems require precise placing and certain skills on the part of operators. The need for operators' participation makes automation impossible. Internal calibrating devices that include optical testing elements are hard to make and require additional beam-splitting plates or switchable optical elements.

The lack in the existing instrument of an adjustment system used for aligning the input pupil of the instrument with the pupil of the eye reduces the precision of measurements, the drawback becoming greater as the order of measured aberrations becomes higher and their magnitude increases.

There are various devises used for adjusting required distances between the ophthalmologic instrument and the eye.

There is a device (U.S. Pat. No. 4,881,807) where the distance between the instrument and the eye is determined by a computer estimating the positions of Purkinje images. The use of a computer makes the instrument and the adjustment procedure significantly more complicated. The problem is the difficulty, for the operator, of finding the working area of the electronic system and determining the direction of misalignment.

The prototype ophthalmologic device used for measuring and operating on patients' eyes (U.S. Pat. No. 5,562,656) is the closest, as concerns the design and purpose, to the substance of this application, that is, the device for adjusting the aberrometer and the aligning method implemented in it.

The existing device includes a light source, a system for projecting the images of marks to a patient's eye, a system for visually controlling the positions of the mark images as related to each other, and a system for three-dimensional positioning of the instrument in relation to the eye. The projecting system includes two projectors placed at an angle to the optical axis of the device creating the images of one or several slots on the cornea. Watching, through a microscope, the positions of these images in relation to each other, one may estimate the distance between the instrument and the eye.

The adjustment method implemented in this device, which is used for measuring and operating, includes illuminating the eye, projecting slot images onto it, visually controlling the positions of these projected slot images and the three-dimensional positioning of the instrument.

The disadvantages of this device and adjustment method include the low precision of measurements because it depends on the forming of the slot images on the cornea and also the limitation of its use, when the light source is weak, by the visible part of the light spectrum which is inconvenient for the patient whose cornea is transparent so observation is possible only because of light scattering. In the infrared zone, the scattered slot images will not be visible on the cornea due to a low contrast. Besides, the design of the marks used in the prototype device does not allow the operator to explicitly determine the direction of misalignment.

SUMMARY OF THE INVENTION

The substance of this application is the following group of inventions under a common title "Aberrometer Provided with a Visual Acuity Testing System".

The two modifications have the same purpose, which is automatically measuring the aberrations of the human eye, determining the subjective visual acuity while, simultaneously, selecting the best spherocylindrical correction in various states of the accommodation of the eye. The second modification also determines the magnitude of the influence of higher-order aberrations on subjective visual acuity while predicting the results of the correction. The implementation of the modifications leads to a single technical result verbally formulated as an increased precision of measurements.

The alignment system is intended for use with the aberrometer.

The method of adjusting the aberrometer is implemented in the alignment system.

The purpose of this group of inventions is creating a more precise ophthalmologic instrument with a large number of functional capabilities, including automatically measuring the aberrations of the human eye, finding out their influence on subjective visual acuity and forecasting the results of correction.

The common technical result, which may be achieved by implementing this group of inventions, is an increased precision of the ophthalmologic instrument.

The principal technical result which may be achieved by implementing the invention entitled "Aberrometer Provided with a Visual Acuity Testing System" in its both modifications is an increased dynamic range of measurements (an increase of the relative precision of measurements) and the capability of examining the eye and determining the clinical visual acuity while, simultaneously, selecting the best spherocylindrical correction and the correction of higher-order aberrations.

The added technical results that may be achieved through various versions and applications of the invention entitled "Aberrometer Provided with a Visual Acuity Testing System" are as follows:

the capability of controlling the applied correction,
the automation of the controls and the maintenance of the instrument in working condition, that is, the elimination of human factor from the adjustment process,
the simplification of the design of the instrument,
the broadening of the functional capabilities of the instrument,
the enhancement of the conditions of the use of the instrument,
the use of the results of measurements for the purpose of vision correction.

The implementation of the design of the compensation measurement system suggested hereby is different from the existing compensators because it allows to do the following:

broaden the functional capabilities of the astigmatism compensator and achieve the automation of its controls,
simplify the design of the ophthalmologic instrument and make its alignment more convenient because of the suggested design and the location of the refraction compensator.

The added technical results achieved through the implementation of the suggested device for adjusting the ophthalmologic instrument include the broadening of the operational capabilities of the device, the creation of more comfortable conditions for patients and the enhanced convenience of servicing the device.

The said technical result, meaning the increased dynamic range of the wavefront sensor used for measuring aberrations is achieved through the following:

The first modification of the instrument is the said device containing a point light source. The light is projected onto the retina and creates a virtual light source on it whose beam is scattered by the retina, then passes through the optical systems of the eye and, in the process, becomes phase modulated, the modulation corresponding to the total optical aberrations of the eye, then passes through the system measuring the shape of the wavefront of the light beam leaving the eye, which is the wavefront sensor whose output is the input of the control system of the instrument. The instrument additionally includes an aberration compensating system placed between the eye and the measuring system. On leaving the eye, the beam from the virtual light source projected onto the retina goes through the compensation system, which consists of a refraction compensator controlling the focusing of the beam dispersed by the retina and an astigmatism compensator located at the same level as the image of the pupil of the eye.

The second modification of the instrument is the said device containing a point light source. The light is projected onto the retina and creates a virtual light source on it whose beam is scattered by the retina, then passes through the optical systems of the eye and, in the process, becomes phase modulated, the modulation corresponding to the total optical aberrations of the eye, then passes through the system measuring the shape of the wavefront of the light beam leaving the eye, which is the wavefront sensor whose output is the input of the control system of the instrument. The instrument additionally includes an aberration compensating system placed between the eye and the measuring system. On leaving the eye, the beam from the virtual light source projected onto the retina goes through the compensation system, which consists of a refraction compensator controlling the focusing of the beam scattered by the retina and an astigmatism compensator located at the same level as the image of the pupil of the eye and a compensator of higher-order aberrations (that is, all of the above plus a compensator of higher-order aberrations).

In the invention which is the substance of this application, along with the standard method of aberration measurement using Shack-Hartman's wavefront sensor, which does not measure aberrations with large and small amplitudes equally well, the method of compensated measurement of aberrations of the eye is implemented. In this method, the beam from the virtual light source goes through the optical mediums and elements of the eye and, before reaching the wavefront sensor, becomes phase-modulated, the modulation corresponding to the sum total of the optical aberrations of the eye. This way, the light beam has a certain amount of aberrations less those compensated (introduced—with the opposite sign—into the beam coming out of the eye by the compensators).

So the aberrations measured by the wavefront sensor and those introduced by the compensator are added up by the computer as the total aberration. The magnitude of aberrations added by the compensators is calculated according to the information passed to the computer by the compensator position sensors.

The refraction compensation unit compensates ametropia within the range between −15 and +10 diopters. The astigmatism compensator works within the range between −6 and +6 diopters. The compensator of higher-order aberrations (a deformable mirror) compensates such aberrations as spherical, coma, etc.

Using data output by compensator position sensors (and data sent by the control device of higher-order aberrations compensator, if there is any), one may determine, with as high a precision as <0.05 diopters, the magnitude of aberrations of the second and higher order introduced by the compensation system. If there are compensators, the wavefront sensor may have a small dynamic range of linear measurements, such as, for instance, from +2 to −2 D, and high sensitivity. The overall dynamic range will be the sum of the dynamic range of the wavefront sensor and that of the compensation.

The broadening of the wavefront sensor's dynamic range of measurement means an increased relative precision of measurements. Practically, a regular instrument will measure 2 D with a precision of 0.05 D, that is, 2.5%. The invention that is the substance of this application allows measuring 15 D with the same precision, that is, 0.3%.

In the suggested design of the aberrometer, the modified Badal's system (refraction compensator) is used for compensating second-order aberrations (defocusing and astigmatism), a system consisting of two cylindrical lenses of opposite signs or two toric lenses of opposite signs, wherein the two cylindrical or two toric (or one toric and one cylindrical) lenses (an astigmatism compensator) are located at the image plane of the input pupil and a system for the precise measurement of the displacements (position sensor) of the movable elements (the displacement of prisms and mirrors in the Badal's system and the turning angles of lenses).

As a rule, a refraction compensator includes a movable prism placed between two lenses. This allows to change the distance between the lenses without moving them. This feature is rather valuable for aberration measurement because the input and output pupils stay in the same places. Because large refraction errors, up to 20 D, sometimes occur, this system is located directly at the input of the instrument. In this case, the further located optical elements deal with beams that are close to being paraxial, which allows to make the design of the instrument simpler.

On the other hand, in order for measurements to be performed, a camera aligned with the optical axis of the instrument must produce an image of the pupil of the eye. This makes necessary the introduction of various beam-splitting elements into the space between the eye and the first lens of the refraction compensator, which decreases the front flange focal length of the instrument (the distance between the eye and the first mechanical or optical element of the instrument).

It is suggested hereby that the refraction compensation system include just one dichroic mirror which also functions as a beam splitter for the adjusting device of the instrument. In this case, the front flange focal distance is increased as compared with the case of a separate beam-splitting plate, which creates an added convenience for both patients and the operator when the instrument is being pointed.

In order to implement this compensation method, the compensator of astigmatism must be placed at the same level as the pupil of the eye. In our case, this level is accessible at the exit point of the refraction compensator (the rear focal level of the 7a lens). If several such levels are available in the instrument, then the location, which is the closest to the entrance of the instrument is preferable, just like in the case of a refraction compensator. In this case the requirements that must be met by the optical element do not need to be too stringent.

Unlike all known compensators of astigmatism where the turning angles of the lenses are dependent and the axis of astigmatism corrector is found by turning the whole instrument around the optical axis of the system, in the suggested design the turning angles of astigmatism corrector lenses are independent and the axis is found by turning the lenses to a required angle. This makes the mechanical drive of the corrector simpler, which, in turn, makes the automation of corrector controls more convenient because there is no need for turning the whole bulky housing. There is no problem calculating the resulting axis and the magnitude of astigmatism when micro-controls are operated.

The compensator of astigmatism includes a couple of cylindrical or toric lenses, which are placed sequentially and may independently turn around its optical axis or there may be a combination of a cylindrical and a toric lenses of opposite curvature signs that may be placed in the same housing. The focal powers of these lenses must comply with the following equation: $k2=-k1/(1-d*k1)$ where d is the distance between the principal planes of the lenses.

In order to exclude chromatic aberrations, the materials the lenses of the astigmatism compensator are made of must have the same dispersion properties.

If the axes of the lenses coincide, the resulting focal power of the whole combination of the lenses equals zero. In this case the combination of the lenses introduces no distortion, which is necessary when the patient has no astigmatism. If the lenses are turned to $\phi1$ and $\phi2$ angles (see FIG. 7), an astigmatic (saddle-like) wavefront with the specified orientation and amplitude is formed, which is necessary when the patient has astigmatism which must be compensated.

The astigmatism corrector is controlled by setting its axis in a position, in relation to that of the aberrometer, in which an astigmatic wavefront with the specified orientation and amplitude is formed in order to correct the distortions on hand.

A system for the precise setting of the initial lens turning angles is necessary for controlling the astigmatism corrector. The angles may be set with a drive controlled by a mechanical, optical or magnetic sensor. The drive must assure the precise angular positioning of the lenses in relation to the initial position determined by the sensor. This may be done with the use, for instance, of a stepping motor with a gear or toothed belt drive assuring the minimal backlash when the direction of rotation is reversed. This device may also be equipped with an angle sensor (optical, magnetic or induction). In this case, precision requirements for the mechanical drive to meet need not to be too stringent, which constitutes an added technical result that may be achieved when implementing this invention.

For a cylindrical waveform to be formed, in case the patient's eye creates distortions that must be compensated, an additional spherical correction is introduced by moving lens 7d.

The astigmatism corrector and refraction compensator are placed between the eye and the test pattern so that the light rays forming the image of the pattern on the retina go through them. The astigmatism corrector and refraction compensator may introduce a phase distortion into the light rays reflected from the test pattern. When this distortion is of the sign opposite to that of the distortion the light acquires while passing through the optical system of the eye, their effects on visual acuity are eliminated. Having then determined the magnitude and topology of the distortions introduced by the compensators, one may use this information for the purpose of correcting vision with eyeglasses, contact lenses, laser ablation, etc.

In the suggested invention, the astigmatism corrector is effective only for the light leaving the eye and the light entering the light after being reflected from the test pattern. It has no effect on the propagation and shape of the wavefront produced by the point light source passing through the astigmatism corrector and refraction compensator because the diameter of this beam is much smaller than that of the eye pupil and the aperture of the astigmatism corrector.

The capability of determining visual acuity while selecting the best spherocylindrical correction through measuring the extent of accommodation is achieved due to that the suggested device also includes a projector of test patterns which, jointly with the refraction and astigmatism compensator (the first modification), or the compensators of refraction astigmatism and higher-order aberrations (the second modification) projects the image of the test pattern on the retina, then refocuses and, following commands from the computer, changes the visible distance to it, that is, introduces an additional refractory correction into the light beam that forms the image. The waveform sensor, following the signal sent by the projector, registers the positions of the refocusing system characterized by the extent of the accommodation of the eye. After that, at a command from the computer, the refocusing system assumes the position corresponding to the image being at infinity and, depending on the selected method of determining visual acuity, its position is changed by the operator and visual acuity is tested by determining the smallest discernible element of the test pattern.

At the upper limit of visual acuity, the computer, following a signal from the waveform sensor, may fine-adjust the astigmatism corrector and refraction compensator (the first modification) or the compensators of refraction astigmatism and higher-order aberrations (the second modification). The patient may manually control correction, trying to achieve the best subjective visual acuity.

Another technical result, the maintenance of the instrument in the workable condition so it may produce veritable and precise data is achieved by the built-in automatic calibration system with a virtual reference light source as a test element. This system allows to precisely measure the current correction level.

The use of a virtual reference light source as a test element, as opposed to optical test elements, makes the design of the instrument simpler and, therefore, allows the automation of its calibration.

One more added technical result, the self-testing capability in the instrument (checking the correctness of the algorithms of the restoration of the wavefront and that of setting calibration coefficients in order to prevent various malfunctions during work (like those in the charge-coupled device of the camera of the waveform sensor or the unsanctioned readjustment of the computer by the operator) is achieved by that the drive of the auto-calibration system is installed on a movable platform with a device precisely measuring all displacements. A displacement of the scatterer from the focal plane leads to the transformation of the flat calibrating wave into a spherical one. The correctness of the calibration of the instrument is checked by measuring the curvature of the wavefront by the sensor (like the Shack-Harman's sensor) and comparing it with the calculated values (in relation to measurable displacements).

The added precision of measurements is achieved by that that the suggested invention includes an additional alignment system assuring the setting of the working distance between the instrument and the eye. This system comprises a system projecting the marks onto the patient's iris, a source of illumination, a system for the visual observation of the mutual positions of the projected images of the marks so that the direction of the movement of the instrument may be determined in order to set the distance between it and the eye. The optical axis of this system lies between the directions of the projections of the images of the marks and coincides with the optical axis of the instrument. There is also a system for three-dimensional displacement of the instrument and/or the eye.

The implementation, in this instrument, of the method when the images of the marks are projected directly onto the iris allows to more precisely align the input pupil of the instrument with the pupil of the eye. This is possible because the plane of the iris practically coincides with the optical pupil of the eye, while the distance between the top of the cornea and the pupil of the eye may considerably vary. When this method is used, the contrast of images is considerably higher even when infrared light is used because the iris is not transparent to infrared light and scatters it very well.

When this method is implemented in the instrument, there is a problem of the blurring of one of the edges of the image because the surface of the iris is inclined in relation to the projector. This problem may be eliminated by the use of a telecentric projection system with a large depth of field and an inclined position of the marks in the projectors in accordance with Scheimpflug's principle (Theodor Scheimpflug's British Patent entitled "An Improved Method and Apparatus for the Systematic Alteration or Distortion of Plane Pictures and Images by Means of Lenses and Mirrors for Photography and for other purposes" (GB 1196/1904)).

Finally, more added technical results, namely, the broadening of the functional capabilities of the ophthalmologic instrument and the creation of more comfortable conditions for patients are achieved by the use of infrared light source for the illumination of the eye and, consequently, the use of an infrared video camera in the system of visual observation.

The increased convenience of this ophthalmologic instrument for the operator is achieved by the use in the adjustment device of special marks of the sector-in-a-circle type. Their design is such that when their images come together at the level of the input pupil of the instrument, a circle divided by cross marks appears. If the distance is larger or smaller then required, this does not happen. The direction of the displacement of the instrument needed for the precise setting of the distance between the eye and the instrument may be easily determined by the way the images look.

BRIEF DESCRIPTION OF THE DRAWINGS

Any of the two modifications of the instrument allows to measure the vertex distance and that between the centers with the use of the system for aligning the instrument that is included in it. The aberrometer is first aligned with the center of one eye, than with the bridge of the nose and finally with the center of the other eye. While this is done, the positions of the instrument are registered with the positioning sensor installed on the movable table of the instrument. This use of the aberrometer broadens its functional capabilities.

DETAILED DESCRIPTION

Below please find information confirming the viability of the group of inventions which are the substance of this application and their ability to function as described.

Figure 1:
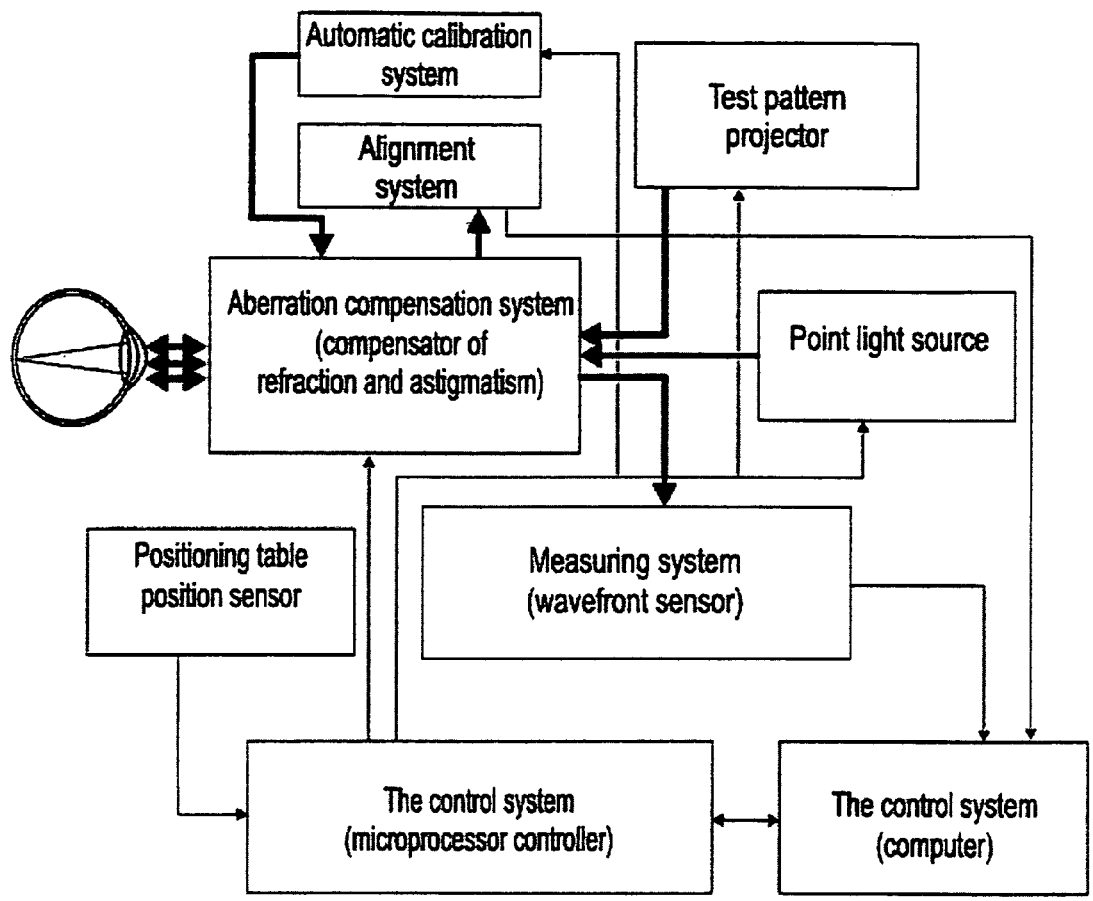
FIG. 1: the structural diagram of the instrument that is the substance of this application (the first modification)
Figure 3:
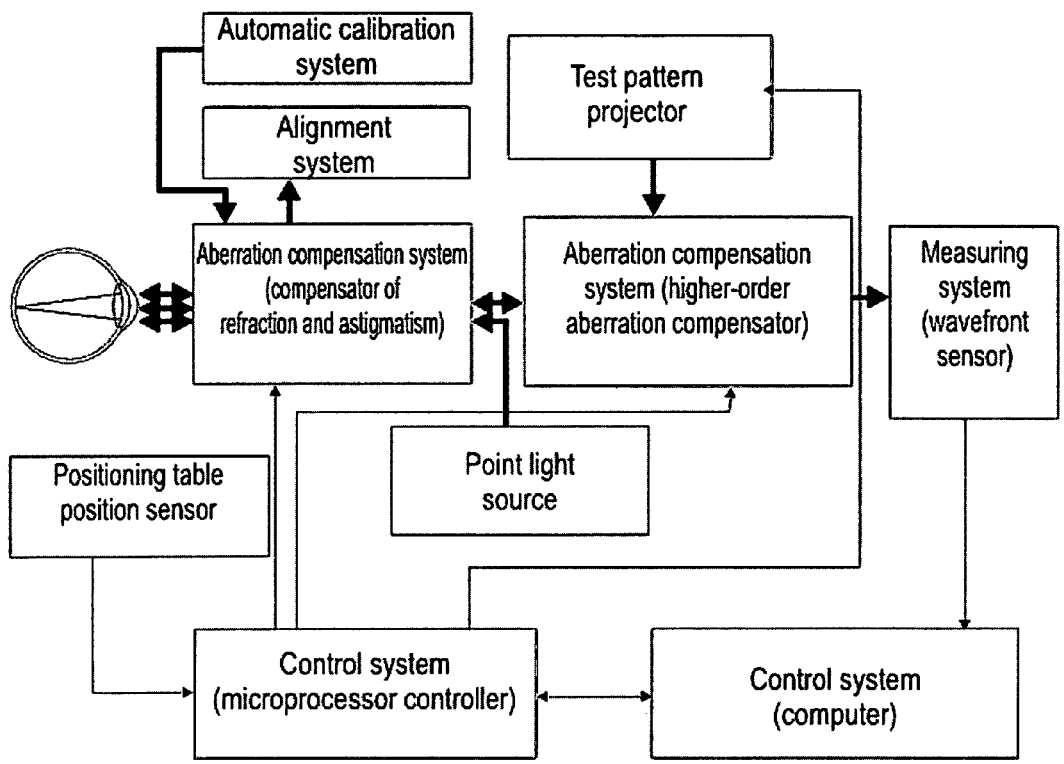
FIG. 3: the structural diagram of the instrument t (the second modification)

The aberrometer with a system for testing visual acuity comprises the following structural units (see FIGS. 1 and 3):
1) a point light source
2) a measuring system based on a wavefront sensor (of the Sack-Hartman type)
3) a system compensating casual aberrations, comprising a refraction and astigmatism compensator and a higher-order aberrations compensator (see FIG. 3)
4) an alignment system (a pointing camera)
5) a projector of test patterns
6) an automatic calibration and self-testing system
7) a control system including a computer and a microprocessor controller The ophthalmologic instrument intended for measuring the aberrations of the human eye and testing visual acuity, which is the substance of this application, is built on the basis of Shack-Hartman's wavefront sensor whose good performance has been practically proven. Of course, other devices, such as the curvature sensor described in *Phase-Diversity Wave-Front Sensing with a Distorted Diffraction Grating* by Paul M. Blanchard, David J. Fisher, Simon C. Woods and Alan H. Greenaway, Applied Optics, Vol. 39 Issue 35 pp. 6649 and 2000.

Figure 2:
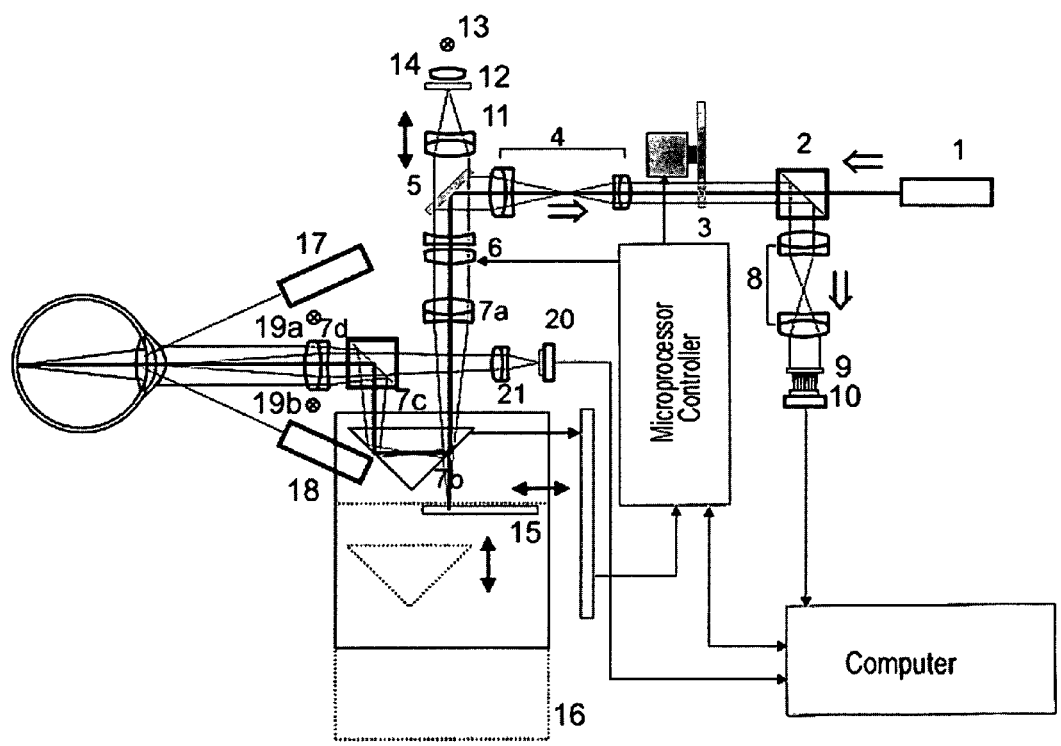
FIG. 2: the optical functional diagram of the instrument (the first modification)
Figure 7:
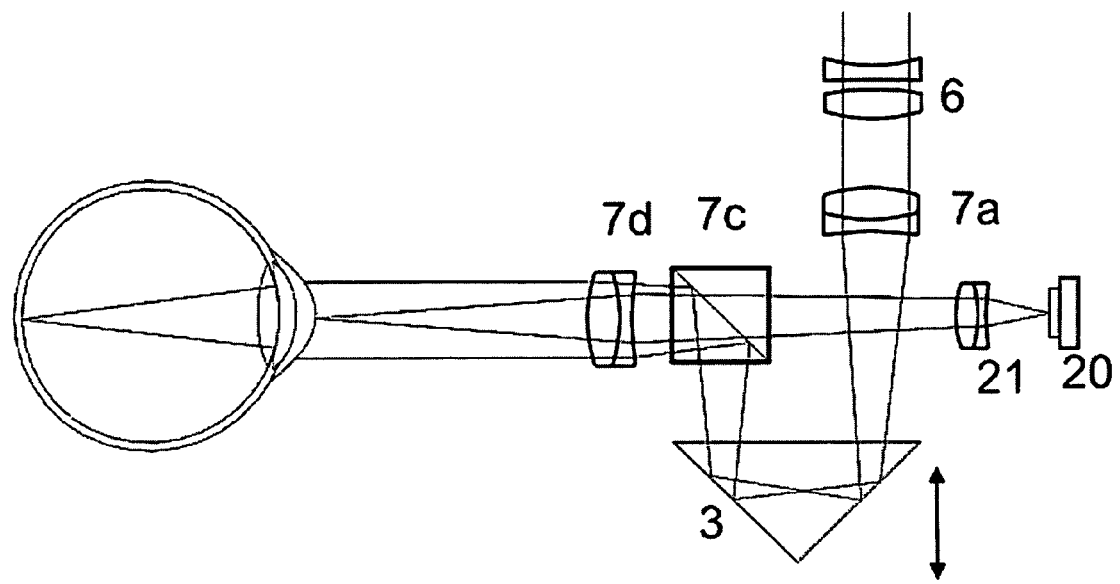
FIG. 7: the optical diagram of the refraction and astigmatism compensator
Figure 7:
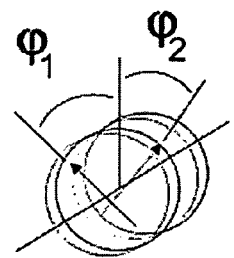

The design and the principle of the functioning of the instrument in its first modification are as follows (see FIGS. 2 and 7):

The light beam thrown by the point light source (1), which may be a semiconductor laser, a super-luminescent diode or a light diode with a small emitting area, producing light with a wavelength between 780 and 850 nm, hits the polarizing beam-splitting cube (2). The laser beam is polarized so as to be fully reflected by the splitting edge of the cube (facing left in FIG. 2). The beam passes through a rotating wedge (3), which performs its circumference-scanning. The scanning angle is about 0.5°. Further, the beam enters a telescopic system that produces an appropriate magnification (4). Having been reflected by the mirror (5) (a spectral splitting plate) the beam passes through the astigmatism compensator (6) comprising two lenses that may independently turn around the optical axis of the instrument. The further located refraction compensator (7), which is a telescope comprising two lenses (7a and 7d), a movable prism (7b) and a spectral beam splitter (7c), controls the focusing of the laser beam. On leaving the instrument, the laser beam enters the patient's eye, then is focused on the retina by the eye's optical elements and creates a virtual reference light source on it. Its light beam, partially scattered by the retina, passes the optical media of the eye in the opposite direction and becomes phase-modulated. The phase modulation of the exiting beam carries information about the total aberrations of the eye that characterize its optical system. This beam passes the said optical elements of the instrument in the opposite direction. However, because the beam thrown back and diffused by the retina is practically not polarized, when it passes the polarizing beam splitter (2), one of the polarization components is reflected from the splitting edge and enters the telescope (2), which is necessary for aligning the input pupil with the plane of the lenslet array (9) of the wavefront sensor (10).

The lenslet array forms a pattern, which is a system of focal spots on the array of a standard CCD (charge-coupled device) or CMOS (complementary metal-oxide semiconductor) of the camera of the sensor, that is, creates a set of images of the virtual light source. The output signal of the sensor is sent from the array to the computer and the latter restores the chart of aberrations and generates signals controlling the compensator of refraction and astigmatism (spherocylindrical corrector). The speed of measuring depends on the speed of the feeding data from the camera into the computer and may reach 100 frames per second. The displacement of spots on the pattern is proportional to the local slopes of the wavefront within the corresponding sub-aperture of the lenslet array. Measuring these displacements, the shape of the wavefront may be restored by the least-squares method. The coordinates of the spots may be determined using the centroid algorithm (J. Lang, B. Grimm, S. Goels, J. Bille, *The Objective measurements of the wave aberrations of the human eye using a Hartman-Shack wavefront sensor*, J. Opt. Soc. Am. A, 11 1949-1957 (1994)). The parameters of the lenslet array are selected so as to make possible the restoration of the wavefront with the precision of ⅛ of the wavelength of the probing beam. The shape of the wavefront may be represented by 36 Zernike polynomials.

The refraction and astigmatism compensator is necessary to correct astigmatic (saddle-like) distortions of the wavefront of the optical light beam with a specified orientation and amplitude.

The refraction compensator (7) (7a-7d) located directly at the instrument's entrance, works as follows. After passing through the first lens (7d) of the refraction compensator, the light beam from the virtual light source, leaving the eye, hits the dichroic beam splitter (7c) that has the shape of a cube or a plate. The beam splitter selectively reflects visible and infrared light generated by the reference point light source (1) but lets through the infrared beam used by the alignment system for illuminating the eye. The reflected beam hits the movable prism (7b) or a system of mirrors and then the second lens (7a) of the compensator. This lens is installed so as not to block the beam generating the image of the eye. The drive of the prism (7b) is equipped with an optical or induction motion sensor and an initial position sensor. The drive of the astigmatism corrector is equipped with the sensor registering the initial positions of the lenses and, possibly, a sensor of angular displacement.

The instrument includes a projector of test patterns used for testing visual acuity while selecting the best spherocylindrical correction which comprises a system of lenses (11) that, together with the refraction and astigmatism compensator and the elements of the eye projects the test pattern (12) onto the retina. The output pupil of the projector is aligned with the plane of astigmatism corrector, which is the principal plane of its system of two cylindrical lenses and, therefore, with the pupil of the eye. The lens system of the projector has moving optical elements allowing to refocus the system so as to make possible the introduction of added defocusing, mostly within the range between −6 and +4 diopters, necessary for changing the visible distance to the test pattern and creating an accommodation stimulus in the patient's eye. The test pattern may be passive (like a slide or a liquid crystal panel) or self-luminous (like a light-emitting diode panel, etc.). If the pattern is passive, there is a need for a light source, such as a light bulb, a light-emitting diode, etc. with an appropriate condenser (14) projecting the image of the light source onto the plane of the astigmatism corrector. Test patterns may be eye-charts with letters, Landolt rings, etc. The patterns may be changeable which may be implemented either mechanically or electronically—with the use of switchable electronic panels. An added zoom lens may be used for gradually changing the visible size of the test pattern. When this is the case, an intermediate variable-scale image is generated at the mounting level of the test pattern.

The test pattern projector functions as follows:

The condenser (14) projects an image of the light source (13) onto the plane of the astigmatism corrector. The test pattern (12) is mounted in the path of the beam thrown by the source. The lens (11) creates an image of the test pattern at an appropriate distance (when the pattern is in its focal plane, the image is created at infinity). The lens may travel along the optical axis, refocusing to the necessary distance. The beam that passes through the lens enters the astigmatism corrector, which may introduce a required astigmatic correction, and goes on through the refraction compensator, which may introduce a required refraction correction. From there, the beam enters the patient's eye. When visual acuity is tested, the aberrometer functions as follows:

In the initial position, the image of the test pattern is focused at infinity. The compensation of refraction (myopia or hypermetropia) is done by the refraction and astigmatism compensator controlled by signals from the waveform sensor. The system of refocusing of the projector of test patterns introduces added defocusing in the range between the minimum and the maximum while the accommodation of the eye is followed by the wavefront sensor. The positions of the refocusing system, at which the eye stops following the changes of the visible distance to the text pattern, are registered. These positions of the refocusing system characterize the extent of accommodation. Further, the system of the refocusing of the test pattern returns to the initial position and, depending on the selected method of testing visual acuity, the refraction compensator is either placed in the position about −1 D away from the positive limit of the accommodation range or stays where it is. After that, visual acuity is tested in the traditional way (the size of the test patterns is changed until the patient can not assuredly discern any symbols). At the top level of visual acuity, the corrector of astigmatism and refraction compensator may be finely adjusted. Besides, the patient may manually control correction from the remote panel, trying to achieve the best subjective visual acuity. The values obtained for the corrector of astigmatism and refraction compensator may be used in the production of contact lenses, eye glasses or when refraction is corrected surgically.

In the aberrometer presented as an example, a built-in automatic calibration system for the astigmatism compensator that is a part of the design is implemented. The automatic calibration system includes the following and functions as follows:

The prism (7b) travels to such a distance that the focal plane of the lens (7a) becomes accessible. An electrical mechanical drive moves a semitransparent screen (15) or another diffuser with reflection coefficient about 4%. A focused beam thrown by the point light source (1) or a laser forms a virtual reference light source on the screen creating a reference wave used for calibrating the system. Because the diameter of the illuminating beam of the reference source is much smaller than those of the apertures of the elements of the optical system, this beam, when passing straight, avoids practically all distortion, that is, the image of the reference source on the screen is practically ideal. The diagram of the orientation of the beam diffused backwards is selected so as to evenly illuminate the apertures of the optical elements of the system. The Hartman's pattern produced by this light source on the CCD array of the sensor camera is compared with the analogous pattern (Hartman's reference pattern) obtained after the removal of the astigmatism compensator from the system (this procedure is done by the manufacturer during the initial calibration of the instrument). The difference between the two patterns allows to measure the profile of the correction introduced by the astigmatism compensator. The current correction values obtained during automatic calibration may be used for the following: a) checking if the instrument is in working condition and b) measuring the profile of the correction of the aberrations of the eye introduced by the astigmatism compensator.

In a different implementation of the automatic calibration device, the end surface of a single-mode laser-illuminated light guide is used instead of the semitransparent screen.

The automation of the calibration and testing of the instrument is implemented through the following sequence of commands sent by the computer:

a diffuser is introduced in to the focal pane of the lens (7a)

the astigmatism compensator is set in its initial position registered by the initial position sensors.

astigmatism compensator is set in its zero position (the introduced astigmatism is close to zero)

the wavefront sensor registers the current pattern and passes the data to the computer the computer calculates the difference between the current and reference patterns, analyses the data and determines if any aberrations are present. Then, if the extent of astigmatism is greater than specified, the astigmatism compensator is adjusted by turning its lenses. The position obtained this way becomes the new zero position of the astigmatism compensator.

In order to check if the algorithms of the restoration of wavefront work correctly and the calibration coefficients are specified correctly, the electrical mechanical drive may be mounted on a movable platform (16) with an optical or other device for the exact measurement of displacements (the platform of the movable prism (7b) may be used for the purpose). In this case, the displacement of the diffuser from the focal plane will result in the transformation of the flat calibration wave (after it passes the lens (7a)) into a spherical one. Measuring the radius of the curvature of the wavefront with the Shack-Hartman's sensor and comparing it with the calculated values (according to the measured displacement), one may check the correctness of the calibration of the instrument.

At the same time, the correctness of the functioning of the computer program used for the restoration of the wavefront and that of the equipment, including the CCD camera of the wavefront sensor, are checked in order to prevent various malfunctions the work may involve, including the unsanctioned altering of the central computer settings by the operator. If the measured data and those calculated according to the displacement of the platform do not match, the program will block the functioning of the instrument.

The automation of the testing of the instrument is implemented through the following sequence of commands sent by the computer:

the diffuser is displaced to the specified distance from the focal plane of the lens (7a)

the displacement is measured by the displacement sensor connected with the diffuser the wavefront sensor registers the current pattern and passes the data to the computer the computer calculates the difference between the current and reference patterns the computer analyses the patterns and the difference and determines if any aberrations and the spherical equivalent of defocusing are present.

If this equivalent corresponds with the specified precision to the spherical equivalent calculated according to the measured displacement of the diffuser, the instrument is considered functional.

Figure 4:
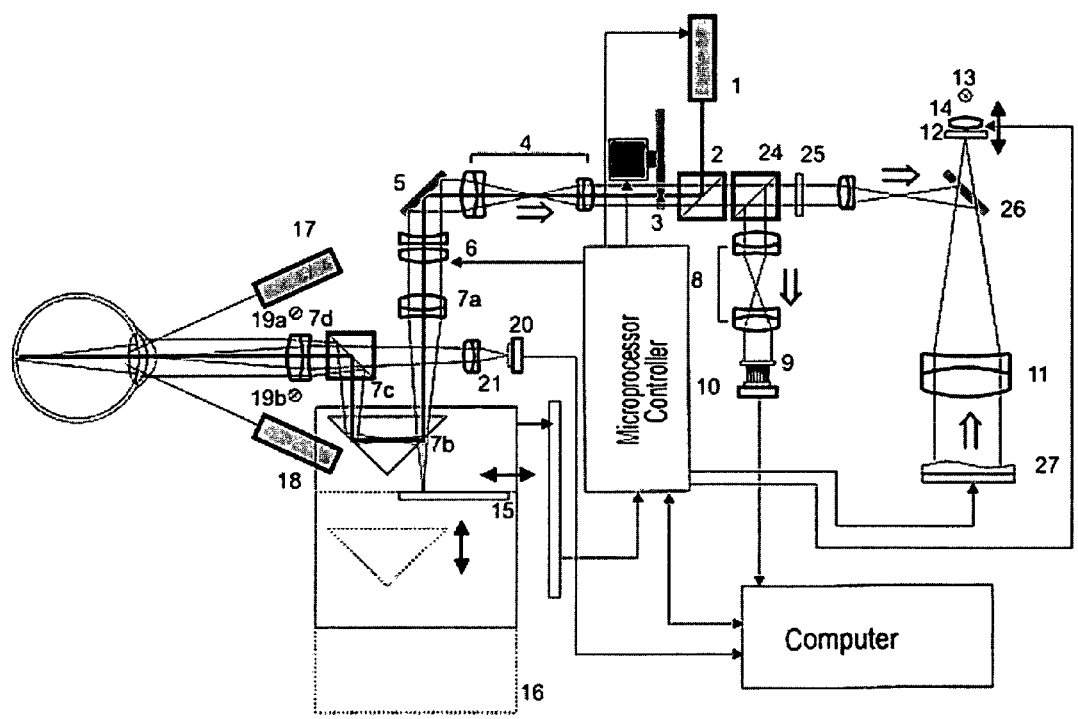
FIG. 4: the optical functional diagram of the instrument (the second modification)

The alignment system (pointing camera) of the aberrometer presented as an example includes (see FIGS. 2 and 4) a projecting system, that is, a mark projector with two identical channels (17) and (18) set at an angle to the optical axis of the instrument, two light sources (19a) and (19b) used for illuminating the eye (these may be light-emitting diodes), a system for visual observation—a video camera (20) whose optical axis is aligned with the optical axis of the instrument, and the lens (21) that, in conjunction with the lens (7b), makes up a multi-component telecentric lens (in the absence of the lens (7b), the image may be produced by the lens of the video camera). Because the eye is illuminated by infrared light, the video camera must be infrared-sensitive. The beam splitter (7c) is used for superimposing the axes of the channels and for measuring. There is no need for the presence of a beam splitter in the adjustment devices of ophthalmologic instruments where adjustment and measuring channels are divided over the area of the input pupil: the input pupil of the pointing system may be made as a ring concentric with the input pupil of the measuring system (or the other way around).

Figure 6:
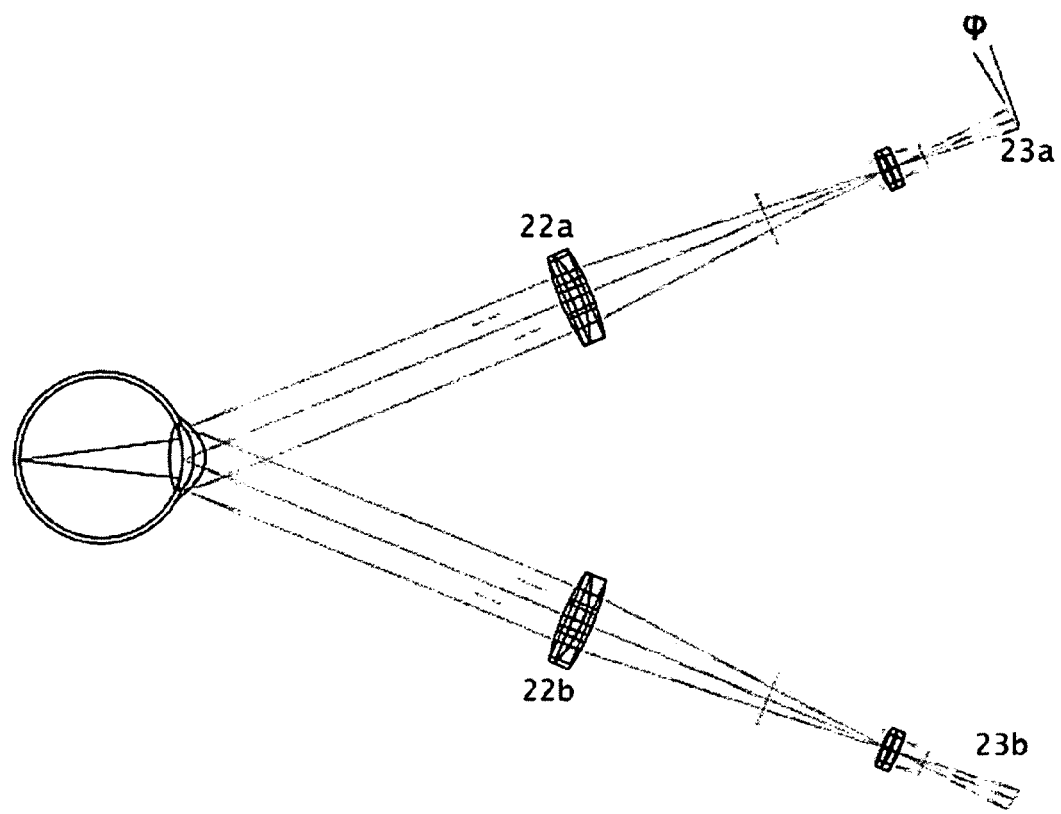
FIG. 6: the optical diagram of the mark projector with the telecentric projecting system

FIG. 6 shows the preferable setup of the mark projector. The lenses (22a) and (22b) make up a telecentric system where the marks (23a) and (23b) are set at an angle other than 90° to the optical axis. This is done in order to compensate for distortions that occur when projecting onto the sloped iris.

The system used for the three-dimensional positioning of the instrument during its adjustment may be made up the same way as the positioning table used in ShL56 and ShL2B slit lamps (see L. S. Urmakher and L. I. Aizenstat, *Ophthalmologic Instruments*, 1988, pp. 111-123). It is worth noting that the system of the three-dimensional positioning of the instrument may be either fully replaced or added to by the system of the displacement, in relation to the instrument, of the patient's eye.

The adjustment of the aberrometer in the infrared is done as follows:

The mark projector projects special sector-in-a-circle images of the marks onto the iris—at an angle to the optical axis of the instrument. The angle and distance between the channels are selected so that the images come together on the plane of the input pupil of the instrument and together make up an image of a circle divided by a cross (see FIG. 5d). At distances greater or less than required, this picture is disrupted (see FIGS. 5c and e). The selection of the angle between the projector channels within the range from 15° to 60° is due to the following consideration: as the angle becomes smaller, pointing sensitivity decreases while larger angles lead to a decreased functional range.

Figure 5:
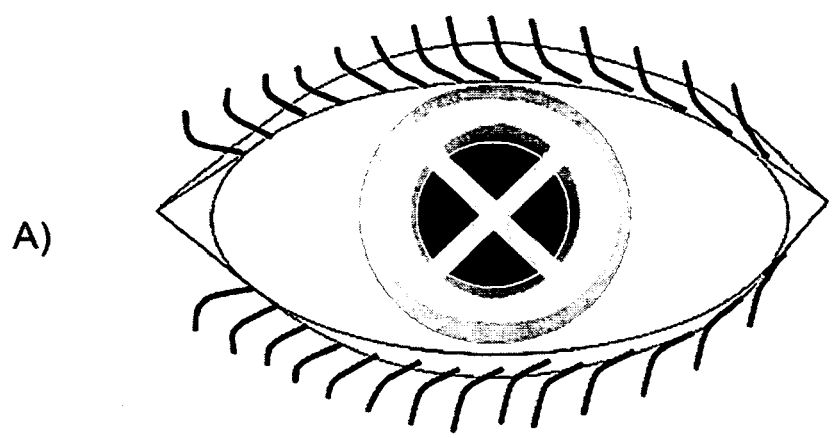
FIG. 5: the diagram of the orientation of the images of the projected marks while the ophthalmologic instrument is adjusted:
   a) the eye placed at a working distance from marks' images projected on the iris
   b) the appearance and orientation of marks for two channels
   c) the misalignment of marks at a distance shorter than the operating one
   d) the misalignment of marks at the operating distance
   e) the misalignment of marks at a distance greater than the operating one
Figure 5:
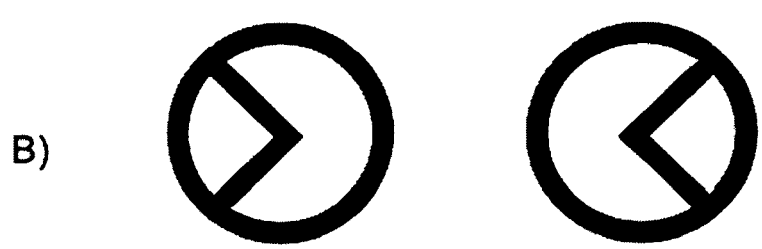
Figure 5:
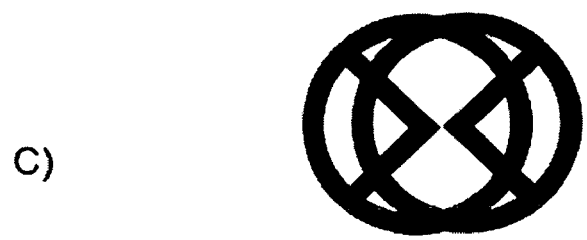
Figure 5:
Figure 5:
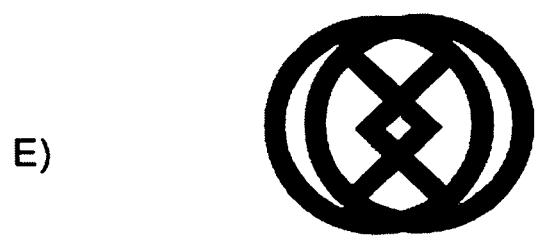

The lens (21) of the video camera creates an image of the eye on the sensor of the video camera (see FIG. 5a). The lens (21) of the video camera creates an image of the patient's eye on the sensor of the camera (see FIG. 5a). The spectral characteristics of the beam splitter (7c) are selected so that infrared beam from the illuminating light-emitting diodes of the adjustment system goes through it without being weakened, while the beam thrown by the reference source and the visible beam from the test pattern projector are fully reflected from it. The direction of the displacement of the instrument may be easily determined by the way the picture looks, which is needed to precisely set the distance to the eye. The image created by the video camera is transmitted to the monitor of the system computer (or a separate video monitor). When adjusting the instrument, the operator tries to bring together the images of the marks projected through the two channels of the projector, which allows to set the proper distance between the instrument and the eye and to align the center of the pupil with the center of the coordinate grid on the monitor.

When the alignment system works in visible light, the beam splitter (7c) must be semitransparent, that is, it must partially reflect and partially transmit visible light. The splitting coefficient is determined by the relative energy sensitivity of the pointing and measuring system.

The description of the design of the aberrometer that is the substance of this application may be considered as an example of the implementation of the method of adjusting the instrument.

The measuring of the inter-pupilary and vertex distances is done as follows:

The setting of the exact parameters of eyeglass correction requires that the distance between the center of the pupils and the vertex distance be known, the latter being the distance between the top of the cornea to the level of eyeglass correction. This distance is, actually the depth between the level of the nose bridge and that of the top of the cornea. The instrument may include a sensor (optical, induction or other) of the displacement of the positioning table, capable of registering and memorizing the trajectory of the positioning table the instrument is installed on. Then the inter-pupilary and vertex distances may be found out by aligning the instrument consecutively with the center of one eye, then with the bridge of the nose and, finally, with the center of the other eye.

The control system of the instrument includes a computer that processes and stores data, restores the aberration chart and controls the instrument following commands coming from the operator and the microprocessor controller.

The design and functioning principle of the second modification of the instrument are different in that one of the polarization components of the beam scattered by the retina, that is practically not polarized, passes through the polarizing beam splitter (2) and hits the added polarizing beam splitter (24) and the quarter-wave plate (25). This plate converts the linearly polarized beam into a circularly polarized one. Then the beam passes through the telescopic system with a turning mirror (26) or a beam splitter. The telescopic system increases the diameter of the beam to between 30 mm and 60 mm, which is necessary for the filling of the aperture of the adaptive mirror (27). Such mirrors are described in the paper entitled *Low-Order Adaptive Deformable Mirror* by J. Christopher Dainty, Alexander V. Koryabin, Alexis V. Kudryashov, Applied Optics, Vol. 37 Issue 21, 1998, p. 4663. The mirror allows to correct the shape of the wavefront it reflects. Having been reflected by the mirror, the beam passes through the telescopic system in the opposite direction and hits the quarter-wave plate. Here, the circularly polarized beam is converted to a linearly polarized one and the vector of its polarization is orthogonal to the vector of the polarization of the beam that went through the plate during the first pass. Accordingly, this downward beam is split by the beam splitter and goes through the telescopic system (8). This telescopic system is necessary for coupling the input pupil of the instrument with the plane of the lenslet array (9) of the waveform sensor (10). The lenslet array forms a pattern that is a system of focal spots on the array of a standard CCD (charge-coupled device) or CMOS (complementary metal oxide semiconductor) of the camera (such as Hitachi KPF-1) of the sensor (that is, creates a set of the images of the virtual source). The output signal of the camera is passed to the computer that restores the aberrations chart and outputs control signals for the refraction, astigmatism (spherocylindrical corrector) and higher-order aberrations compensators.

The instrument in its second modification also includes a projector of test patterns that are sent by the optical elements of the instrument to the retina, passing, on the way there, through the spherocylindrical corrector (the refraction and astigmatism compensator) and the compensator of higher-order aberrations. The design and functioning principle of the test pattern projector are practically the same as in the first modification of the instrument, except that here the lens of the projector (11) is also the second lens of the telescope that couples the plane of the adaptive mirror (27) with that of the pupil of the eye. Besides, there is no need to use one more imaging system because an additional image plane (coupled with the retina) is available. In this case, the test pattern itself may be placed on a movable platform. The displacement of the platform must assure the same range of added refraction in the device. At the upper limit of visual acuity, the astigmatism corrector, refraction compensator and the shape of the adaptive mirror may be fine-adjusted. The patient may control correction, trying to achieve the best subjective visual acuity. The determined values for the astigmatism corrector, refraction compensator and the shape of the adaptive mirror may be used in the production of contact lenses, eyeglasses and during refraction-correcting operations. The corrector of higher-order aberrations (the adaptive mirror) may be used for generating random, changing in time phase distortions, which makes the accommodation of the eye on the test pattern impossible and relaxes the muscles responsible for accommodation.

In the second modification of the instrument, an analogous system of internal calibration is included. It serves for the initial setting of the higher-order aberrations compensator in its zero position. The same system is also used for changing the profile of the higher-order aberrations compensator when the best subjective visual acuity is achieved manually or automatically.

The above information shows that the following conditions are met while using the group of inventions that is the substance of this application:

The invention which is the substance of this application, in its both modifications, is intended for use in medical industry, namely for measuring the aberrations of the human eye while testing subjective visual acuity and, simultaneously, selecting the best spherocylindrical correction. It also serves to find out the effects of higher-order aberrations on subjective visual acuity and prognosticate the results of visual correction.

The way the group of inventions that is the substance of this application is characterized by the claims accounted for by the author, confirms its usability and implementability through the means and methods described herein or known previously.

That is, the group of inventions that is the substance of this application meets the condition of its industrial usability.

What is claimed:

1. An opthalmologic instrument for measuring aberrations of a human eye, comprising:
   a point light source which is projected onto a retina of the eye to create a virtual light source thereon, wherein radiation of the virtual light source is scattered by the retina and then passes through optical systems of the eye and becomes phase-modulated, and wherein the modulation corresponds to a total of optical aberrations of the eye;
   a measuring system for measuring a shape of a wavefront of the radiation leaving the eye, and outputting an output signal to a control system of the instrument;
   a system for compensating for said aberrations, located between the eye and the measuring system and transmitting the radiation leaving the eye, wherein said system comprises a refraction compensator that controls focusing of the radiation scattered by the retina and an astigmatism compensator located at an image plane of a pupil of the eye, wherein the astigmatism compensator comprises: (i) one of two cylindrical lenses of opposite signs and two toric lenses of opposite signs, wherein said lenses are independently rotatable around an optical axis of the compensator, and (ii) a system for setting initial turning angles of said lenses; and
   a projector of test patterns, which, jointly with said refraction compensator and astigmatism compensator, projects an image of a test pattern onto the retina.

2. The instrument of claim 1, wherein the refraction compensator comprises a movable prism and a dichroic mirror which are placed between two lenses, and wherein said dichroic mirror is operable as a beam-splitter to align the instrument.

3. The instrument of claim 1, further comprising a built-in automatic calibration system which uses an additional virtual light source as a test element to measure current positions of the compensators.

4. The instrument of claim 1, further comprising an alignment system which adjusts a proper distance between the eye and the instrument.

5. An opthalmologic instrument for measuring aberrations of a human eye, comprising:
   a point light source which is projected onto a retina of the eye to create a virtual light source thereon, wherein radiation of the virtual light source is scattered by the retina and then passes through optical systems of the eye and becomes phase-modulated, and wherein the modulation corresponds to a total of optical aberrations of the eye;
   a measuring system for measuring a shape of a wavefront of the radiation leaving the eye, and outputting an output signal to a control system of the instrument;
   a system for compensating for said aberrations, located between the eye and the measuring system and transmitting the radiation leaving the eye, wherein said system comprises a refraction compensator that controls focusing of the radiation scattered by the retina, an astigmatism compensator located at an image plane of a pupil of the eye, and a compensator of high-order aberrations, wherein the astigmatism compensator comprises: (i) one of two cylindrical lenses of opposite signs and two toric lenses of opposite signs, wherein said lenses are independently rotatable around an optical axis of the compensator, and (ii) a system for setting initial turning angles of said lenses; and
   a projector of test patterns, which, jointly with said refraction compensator, astigmatism compensator and compensator of high-order aberrations, projects an image of a test pattern onto the retina.

6. The instrument of claim 5, wherein the refraction compensator comprises a movable prism and a dichroic mirror which are placed between two lenses, and wherein said dichroic mirror is operable as a beam-splitter to align the instrument.

7. The instrument of claim 5, further comprising a built-in automatic calibration system which uses an additional virtual light source as a test element to measure current positions of the compensators.

8. The instrument of claim 5, further comprising an alignment system which adjusts a proper distance between the eye and the instrument.

* * * * *